(12) United States Patent
Boussarie et al.

(10) Patent No.: US 11,746,073 B2
(45) Date of Patent: Sep. 5, 2023

(54) METHOD FOR PURIFYING 1-CHLORO-3,3,3-TRIFLUOROPROPENE

(71) Applicant: ARKEMA FRANCE, Colombes (FR)

(72) Inventors: Emmanuel Boussarie, Pierre-Benite (FR); Kevin Hisler, Pierre-Benite (FR); Anne Pigamo, Pierre-Benite (FR); Bertrand Collier, Pierre-Benite (FR)

(73) Assignee: Arkema France, Colombes (FR)

( * ) Notice: Subject to any disclaimer, the term of this patent is extended or adjusted under 35 U.S.C. 154(b) by 149 days.

(21) Appl. No.: 17/600,179

(22) PCT Filed: Apr. 1, 2020

(86) PCT No.: PCT/EP2020/059231
§ 371 (c)(1),
(2) Date: Sep. 30, 2021

(87) PCT Pub. No.: WO2020/201340
PCT Pub. Date: Oct. 8, 2020

(65) Prior Publication Data
US 2022/0153665 A1 May 19, 2022

(30) Foreign Application Priority Data
Apr. 3, 2019 (FR) .................. FR1903536

(51) Int. Cl.
*C07C 17/395* (2006.01)
*C07C 17/20* (2006.01)

(52) U.S. Cl.
CPC .......... *C07C 17/395* (2013.01); *C07C 17/206* (2013.01)

(58) Field of Classification Search
CPC ...... C07C 17/395; C07C 17/206; C07C 21/18
See application file for complete search history.

(56) References Cited

U.S. PATENT DOCUMENTS

| | | | |
|---|---|---|---|
| 6,166,274 | A | 12/2000 | Chen et al. |
| 2002/0198418 | A1 | 12/2002 | Jorda et al. |
| 2004/0033892 | A1 | 2/2004 | Bonnet et al. |
| 2014/0275662 | A1 | 9/2014 | Kopkalli et al. |
| 2015/0203424 | A1 | 7/2015 | Okamoto et al. |
| 2018/0346396 | A1 | 12/2018 | Pigamo et al. |

FOREIGN PATENT DOCUMENTS

| | | |
|---|---|---|
| EP | 1130010 A1 | 9/2001 |
| FR | 926601 A | 10/1947 |
| WO | 0181353 A1 | 11/2001 |
| WO | 2014010530 A1 | 1/2014 |
| WO | 2014099464 A1 | 6/2014 |
| WO | 2014189674 A1 | 11/2014 |
| WO | 2015167784 A1 | 11/2015 |
| WO | 2016148957 A1 | 9/2016 |
| WO | 2017031406 A1 | 2/2017 |
| WO | 2017050686 A1 | 3/2017 |

OTHER PUBLICATIONS

ISA/EP; International Search Report and Written Opinion for International Patent Application No. PCT/EP2020/059231 dated Jun. 19, 2020, 11 pages.

*Primary Examiner* — Jafar F Parsa
(74) *Attorney, Agent, or Firm* — NK Patent Law

(57) ABSTRACT

The present invention relates to a process for purifying 1-chloro-3,3,3-trifluoropropene comprising the steps of: a) providing a stream comprising 1-chloro-3,3,3-trifluoropropene and at least one compound of formula HX wherein X is F or Cl; b) bringing the stream from step a) into contact with a solution A comprising at least one sulfite salt of formula $Y^{n+}_m SO_3$ wherein Y is an alkali or alkaline-earth metal, n=1 or 2, and m=2 when n=1 or m=1 when n=2; in order to form a neutralized stream A1 comprising 1-chloro-3,3,3-trifluoropropene.

12 Claims, No Drawings

METHOD FOR PURIFYING 1-CHLORO-3,3,3-TRIFLUOROPROPENE

CROSS-REFERENCE TO RELATED APPLICATIONS

This application is a U.S. National Stage application of International Patent Application No. PCT/EP2020/059231, filed on Apr. 1, 2020, which claims the benefit of French Patent Application No. FR1903536, filed on Apr. 3, 2019.

TECHNICAL FIELD OF THE INVENTION

The present invention relates to a process for purifying hydrochlorofluoroolefins. In particular, the present invention relates to a process for purifying 1-chloro-3,3,3-trifluoropropene.

TECHNOLOGICAL BACKGROUND OF THE INVENTION 3,3,3-Trifluoro-1-chloropropene, or alternatively 1-chloro-3,3,3-trifluoropropene (HCFO-1233zd), exists in the form of two isomers: the cis isomer, namely Z-3,3,3-trifluoro-1-chloropropene (HCFO-1233zdZ), and the trans isomer, namely E-3,3,3-trifluoro-1-chloropropene (HCFO-1233zdE). They have different boiling points of, respectively, 18.5° C. for the trans compound and 39.5° C. for the cis compound.

Fluids based on E-3,3,3-trifluoro-1-chloropropene (HCFO-1233zdE) have found numerous applications in varied industrial fields, in particular as heat transfer fluids, propellants, foaming agents, blowing agents, gaseous dielectrics, monomers or polymerization media, support fluids, abrasive agents, drying agents, and fluids for energy production units.

The production of HCFO-1233zdE is accompanied by a multitude of by-products having a boiling point close to that of HCFO-1233zdE. This results in purification steps which are relatively complex and costly. The difficulties encountered during the purification of HCFO-1233zdE generally entail an appreciable loss of target product. In addition, the by-products may form azeotropic compositions with the HCFO-1233zdE, making separation by simple distillation very difficult, or even impossible. The purification steps include in particular a step of neutralizing the crude product at the outlet of the reactor in order to remove the residual traces of acids, i.e. HCl and HF. This neutralization step is generally carried out by means of a basic solution.

Known in particular from WO 2015/167784 is a process for separating HCFO-1233zd and HF by a series of steps including, for example, a distillation in order to remove the HCl at the top of the distillation column, the cooling of the stream at the bottom of the column in order to obtain a two-phase mixture, the separation of the two phases and the treatment of one of said phases with an adsorbent which may be a liquid adsorbent (water, NaOH or KOH).

Also known from WO 2016/148957 is a process for purifying HCFO-1233zdE comprising a washing step, a condensation and phase separation step and, finally, a drying step. Also known from WO 2014/010530, WO 2014/189674 and WO 2014/099464 is a process for preparing HCFO-1233zd comprising a purification step such as washing with water or washing with a basic solution.

During the purification of HCFO-1233zd, the treatment carried out in order to remove acidic impurities such as HF or HCl may contribute to the formation of certain impurities. Thus, new acid impurity neutralization conditions must be implemented in order to minimize the degradation of HCFO-1233zd. There is a need for an efficient process for purifying trans-1-chloro-3,3,3-trifluoropropene which minimizes the production of by-products or other impurities resulting from a dehydrochlorination reaction.

SUMMARY OF THE INVENTION

According to a first aspect, the present invention relates to a process for purifying 1-chloro-3,3,3-trifluoropropene comprising the steps of:

a) providing a stream comprising 1-chloro-3,3,3-trifluoropropene and at least one compound of formula HX wherein X is F or Cl;

b) bringing the stream from step a) into contact with a solution A comprising at least one alkali metal hydroxide or one alkaline-earth metal hydroxide and at least one sulfite salt of formula $Y^{n+}{}_m SO_3$ wherein Y is an alkali or alkaline-earth metal, n=1 or 2, and m=2 when n=1 or m=1 when n=2; in order to form a neutralized stream A1 comprising 1-chloro-3,3,3-trifluoropropene.

According to one preferred embodiment, said at least one sulfite salt is selected from the group consisting of $Na_2SO_3$, $K_2SO_3$, $Li_2SO_3$, $CaSO_3$ and $MgSO_3$ or a mixture thereof.

According to one preferred embodiment, said at least one sulfite salt is $Na_2SO_3$ or $K_2SO_3$ or a mixture of both.

According to one preferred embodiment, said solution A comprises at least one alkali metal hydroxide, preferably NaOH.

According to one preferred embodiment, said solution A of step b) comprises a mixture of NaOH and $Na_2SO_3$.

According to one preferred embodiment, said solution A of step b) is an aqueous solution.

According to one preferred embodiment, the content of said at least one sulfite salt is between 2 and 25% by weight based on the total weight of said solution A.

According to one preferred embodiment, step b) is carried out at a temperature of 10° C. to 70° C.

According to one preferred embodiment, the content of alkali metal hydroxide or alkaline-earth metal hydroxide is between 2 and 25% by weight based on the total weight of said solution A.

According to one preferred embodiment, step b) is carried out with an aqueous solution A comprising from 3 to 10% of $Na_2SO_3$ and from 3 to 10% NaOH; and at a temperature of from 20° C. to 60° C.

According to one preferred embodiment, in the stream provided in step a), the molar ratio between the trans isomer and the cis isomer of 1-chloro-3,3,3-trifluoropropene is from 2:1 to 50:1, preferably 5:1 to 50:1, in particular 9:1 to 50:1.

Preferably, the present process relates to a process for purifying trans-1-chloro-3,3,3-trifluoropropene comprising the steps of:

a) providing a stream comprising trans-1-chloro-3,3,3-trifluoropropene and at least one compound of formula HX wherein X is F or Cl;

b) bringing the stream from step a) into contact with a solution A comprising at least one alkali metal hydroxide or one alkaline-earth metal hydroxide and at least one sulfite salt of formula $Y^{n+}{}_m SO_3$ wherein Y is an alkali or alkaline-earth metal, n=1 or 2, and m=2 when n=1 or m=1 when n=2; in order to form a neutralized stream A1 comprising trans-1-chloro-3,3,3-trifluoropropene.

According to a second aspect, the present invention provides a process for producing 1-chloro-3,3,3-trifluoropropene comprising the steps of:

i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream B comprising 1-chloro-3,3,3-trifluoropropene, HF and/or HCl;

ii) carrying out the process for purifying 1-chloro-3,3,3-trifluoropropene according to the present invention using a stream comprising 1-chloro-3,3,3-trifluoropropene, HF and/or HCl.

DETAILED DESCRIPTION OF THE PRESENT INVENTION

According to a first aspect, the present invention relates to a process for purifying 1-chloro-3,3,3-trifluoropropene, preferably trans-1-chloro-3,3,3-trifluoropropene.

According to one preferred embodiment, said purification process comprises:

a) providing a stream comprising 1-chloro-3,3,3-trifluoropropene and at least one compound of formula HX wherein X is F or Cl;

b) bringing the stream from step a) into contact with a solution A comprising at least one alkali metal hydroxide or one alkaline-earth metal hydroxide and at least one sulfite salt of formula $Y^{n+}_m SO_3$ wherein Y is an alkali or alkaline-earth metal, n=1 or 2, and m=2 when n=1 or m=1 when n=2; in order to form a neutralized stream A1 comprising 1-chloro-3,3,3-trifluoropropene.

According to one particular embodiment, said purification process comprises:

a) providing a stream comprising trans-1-chloro-3,3,3-trifluoropropene and at least one compound of formula HX wherein X is F or Cl;

b) bringing the stream from step a) into contact with a solution A comprising at least one alkali metal hydroxide or one alkaline-earth metal hydroxide and at least one sulfite salt of formula $Y^{n+}_m SO_3$ wherein Y is an alkali or alkaline-earth metal, n=1 or 2, and m=2 when n=1 or m=1 when n=2; in order to form a neutralized stream A1 comprising trans-1-chloro-3,3,3-trifluoropropene.

The applicant has observed in particular that the use of a sulfite salt of formula $Y^{n+}_m SO_3$ as defined above makes it possible to limit the formation of impurities during step b). These impurities can result from the degradation of 1-chloro-3,3,3-trifluoropropene, of the cis isomer and/or of the trans isomer, or optionally from other compounds present in the starting stream, during step b). This step allows the neutralization of the compound(s) of formula HX as defined above. The present purification process thus makes it possible to recover a stream A1 comprising 1-chloro-3,3,3-trifluoropropene, preferably trans-1-chloro-3,3,3-trifluoropropene, wherein the content of compound of formula HX is greatly reduced, while limiting the formation of additional impurities. Among the additional impurities, mention may in particular be made of trifluoropropyne, the presence of which is disadvantageous. Preferably, the compound HX is HCl or HF or a mixture thereof.

The stream provided in step a) can comprise a mixture of cis/trans isomers of 1-chloro-3,3,3-trifluoropropene. Preferably, in the stream provided in step a), the molar ratio between the trans and cis isomer of 1-chloro-3,3,3-trifluoropropene is from 2:1 to 50:1, preferably 5:1 to 50:1, in particular 9:1 to 50:1. In addition, the stream provided in step a) may optionally comprise 1,3,3,3-tetrafluoropropene and 1,1,1,3,3-pentafluoropropane, in contents explained below in the present application in relation to the stream B.

Preferably, said at least one sulfite salt of formula $Y^{n+}_m SO_3$ is selected from the group consisting of $Na_2SO_3$, $K_2SO_3$, $Li_2SO_3$, $CaSO_3$ and $MgSO_3$ or a mixture thereof. More preferentially, said at least one sulfite salt of formula $Y^{n+}_m SO_3$ is $Na_2SO_3$ or $K_2SO_3$ or a mixture thereof. In particular, said at least one sulfite salt of formula $Y^{n+}_m SO_3$ is $Na_2SO_3$.

Preferably, the content in said at least one sulfite salt in said solution A is between 1% and 50% by weight, more preferentially between 2% and 40% by weight, in particular between 2% and 30%, more particularly between 2% and 25% by weight based on the total weight of said solution A.

As mentioned above, said solution A of step b) comprises at least one alkali metal hydroxide or one alkaline-earth metal hydroxide, or a mixture of the two, in addition to said salt of formula $Y^{n+}_m SO_3$ as defined above. The alkali metal hydroxide may be NaOH or KOH. The alkaline-earth metal hydroxide may be $Ca(OH)_2$ or $Mg(OH)_2$. Preferably, the content of said at least one alkali or alkaline-earth metal hydroxide in said solution A is between 1% and 50% by weight, more preferentially between 2% and 40% by weight, in particular between 2% and 30%, more particularly between 2% and 25% by weight based on the total weight of said solution A.

Preferably, said solution A of step b) is a solution comprising a salt of formula $Y^{n+}_m SO_3$ and NaOH or a salt of formula $Y^{n+}_m SO_3$ and KOH or a salt of formula $Y^{n+}_m SO_3$, NaOH and KOH. In particular, said solution A of step b) is a solution comprising $Na_2SO_3$ and NaOH or $Na_2SO_3$ and KOH or $Na_2SO_3$, NaOH and KOH.

Preferably, said solution A of step b) is an aqueous solution comprising a salt of formula $Y^{n+}_m SO_3$ and NaOH or a salt of formula $Y^{2+}_m SO_3$ and KOH or a salt of formula $Y^{n+}_m SO_3$, NaOH and KOH. In particular, said solution A of step b) is an aqueous solution comprising $Na_2SO_3$ and NaOH or $Na_2SO_3$ and KOH or $Na_2SO_3$, NaOH and KOH.

Preferably, said solution A of step b) comprises between 1% and 50% by weight, more preferentially between 2% and 40% by weight, in particular between 2% and 30%, more particularly between 2% and 25% of a salt of formula $Y^{n+}_m SO_3$ and between 1% and 50% by weight, more preferentially between 2% and 40% by weight, in particular between 2% and 30%, more particularly between 2% and 25% of NaOH. According to another preferential embodiment, said solution A of step b) comprises between 1% and 50% by weight, more preferentially between 2% and 40% by weight, in particular between 2% and 30%, more particularly between 2% and 25% of a salt of formula $Y^{n+}_m SO_3$ and between 1% and 50% by weight, more preferentially between 2% and 40% by weight, in particular between 2% and 30%, more particularly between 2% and 25% of KOH. According to another preferential embodiment, said solution A of step b) comprises between 1% and 50% by weight, more preferentially between 2% and 40% by weight, in particular between 2% and 30%, more particularly between 2% and 25% of a salt of formula $Y^{n+}_m SO_3$; between 1% and 50% by weight, more preferentially between 2% and 40% by weight, in particular between 2% and 30%, more particularly between 2% and 25% of NaOH and between 1% and 50% by weight, more preferentially between 2% and 40% by weight, in particular between 2% and 30%, more particularly between 2% and 25% of KOH.

Preferably, said solution A of step b) is an aqueous solution comprising between 1% and 50% by weight, more preferentially between 2% and 40% by weight, in particular between 2% and 30%, more particularly between 2% and 25% of a salt of formula $Y^{n+}_m SO_3$ and between 1% and 50% by weight, more preferentially between 2% and 40% by weight, in particular between 2% and 30%, more particularly between 2% and 25% of NaOH. According to another preferential embodiment, said solution A of step b) is an aqueous solution comprising between 1% and 50% by weight, more preferentially between 2% and 40% by weight, in particular between 2% and 30%, more particularly between 2% and 25% of a salt of formula $Y^{n+}{}_m SO_3$ and between 1% and 50% by weight, more preferentially between 2% and 40% by weight, in particular between 2% and 30%, more particularly between 2% and 25% of KOH. According to another preferential embodiment, said solution A of step b) is an aqueous solution comprising between 1% and 50% by weight, more preferentially between 2% and 40% by weight, in particular between 2% and 30%, more particularly between 2% and 25% of a salt of formula $Y^{n+}{}_m SO_3$; between 1% and 50% by weight, more preferentially between 2% and 40% by weight, in particular between 2% and 30%, more particularly between 2% and 25% of NaOH and between 1% and 50% by weight, more preferentially between 2% and 40% by weight, in particular between 2% and 30%, more particularly between 2% and 25% of KOH.

Preferably, said solution A of step b) comprises between 1% and 50% by weight, more preferentially between 2% and 40% by weight, in particular between 2% and 30%, more particularly between 2% and 25% of $Na_2SO_3$, and between 1% and 50% by weight, more preferentially between 2% and 40% by weight, in particular between 2% and 30%, more particularly between 2% and 25% of NaOH. According to another preferential embodiment, said solution A of step b) comprises between 1% and 50% by weight, more preferentially between 2% and 40% by weight, in particular between 2% and 30%, more particularly between 2% and 25% of a salt of $Na_2SO_3$ and between 1% and 50% by weight, more preferentially between 2% and 40% by weight, in particular between 2% and 30%, more particularly between 2% and 25% of KOH. According to another preferential embodiment, said solution A of step b) comprises between 1% and 50% by weight, more preferentially between 2% and 40% by weight, in particular between 2% and 30%, more particularly between 2% and 25% of $Na_2SO_3$; between 1% and 50% by weight, more preferentially between 2% and 40% by weight, in particular between 2% and 30%, more particularly between 2% and 25% of NaOH and between 1% and 50% by weight, more preferentially between 2% and 40% by weight, in particular between 2% and 30%, more particularly between 2% and 25% of KOH.

Preferably, said solution A of step b) is an aqueous solution comprising between 1% and 50% by weight, more preferentially between 2% and 40% by weight, in particular between 2% and 30%, more particularly between 2% and 25% of $Na_2SO_3$, and between 1% and 50% by weight, more preferentially between 2% and 40% by weight, in particular between 2% and 30%, more particularly between 2% and 25% of NaOH. According to another preferential embodiment, said solution A of step b) is an aqueous solution comprising between 1% and 50% by weight, more preferentially between 2% and 40% by weight, in particular between 2% and 30%, more particularly between 2% and 25% of $Na_2SO_3$ and between 1% and 50% by weight, more preferentially between 2% and 40% by weight, in particular between 2% and 30%, more particularly between 2% and 25% of KOH. According to another preferential embodiment, said solution A of step b) is an aqueous solution comprising between 1% and 50% by weight, more preferentially between 2% and 40% by weight, in particular between 2% and 30%, more particularly between 2% and 25% of $Na_2SO_3$; between 1% and 50% by weight, more preferentially between 2% and 40% by weight, in particular between 2% and 30%, more particularly between 2% and 25% of NaOH and between 1% and 50% by weight, more preferentially between 2% and 40% by weight, in particular between 2% and 30%, more particularly between 2% and 25% of KOH.

Preferably, step b) of the present process is carried out at a temperature of from 10° C. to 90° C., advantageously from 10° C. to 80° C., preferably from 10° C. to 70° C., in particular 10° C. to 60° C. Thus, according to one preferred embodiment, step b) is carried out with a solution A comprising between 1% and 50% by weight, more preferably between 2% and 40% by weight, in particular between 2% and 30%, more particularly between 2% and 25% of a salt of formula $Y^{n+}{}_m SO_3$ and between 1% and 50% by weight, more preferentially between 2% and 40% by weight, in particular between 2% and 30%, more particularly between 2% and 25% of NaOH; at a temperature of from 10° C. to 90° C., advantageously from 10° C. to 80° C., preferably from 10° C. to 70° C., in particular from 10° C. to 60° C. According to one particular embodiment, step b) is carried out with a solution A comprising between 1% and 50% by weight, more preferentially between 2% and 40% by weight, in particular between 2% and 30%, more particularly between 2% and 25% of a salt of formula $Na_2SO_3$ and between 1% and 50% by weight, more preferentially between 2% and 40% by weight, in particular between 2% and 30%, more particularly between 2% and 25% of NaOH; at a temperature of from 10° C. to 90° C., advantageously from 10° C. to 80° C., preferably from 10° C. to 70° C., in particular from 10° C. to 60° C.

According to one preferred embodiment, step b) is carried out with a solution A comprising between 1% and 50% by weight, more preferably between 2% and 40% by weight, in particular between 2% and 30%, more particularly between 2% and 25% of a salt of formula $Y^{n+}{}_m SO_3$ and between 1% and 50% by weight, more preferentially between 2% and 40% by weight, in particular between 2% and 30%, more particularly between 2% and 25% of KOH; at a temperature of from 10° C. to 90° C., advantageously from 10° C. to 80° C., preferably from 10° C. to 70° C., in particular from 10° C. to 60° C. According to one particular embodiment, step b) is carried out with a solution A comprising between 1% and 50% by weight, more preferentially between 2% and 40% by weight, in particular between 2% and 30%, more particularly between 2% and 25% of a salt of formula $Na_2SO_3$ and between 1% and 50% by weight, more preferentially between 2% and 40% by weight, in particular between 2% and 30%, more particularly between 2% and 25% of KOH; at a temperature of from 10° C. to 90° C., advantageously from 10° C. to 80° C., preferably from 10° C. to 70° C., in particular from 10° C. to 60° C.

According to another preferred embodiment, step b) is carried out with a solution A comprising between 1% and 50% by weight, more preferably between 2% and 40% by weight, in particular between 2% and 30%, more particularly between 2% and 25% of a salt of formula $Y^{n+}{}_m SO_3$; between 1% and 50% by weight, more preferentially between 2% and 40% by weight, in particular between 2% and 30%, more particularly between 2% and 25% of KOH and between 1% and 50% by weight, more preferentially between 2% and 40% by weight, in particular between 2% and 30%, more particularly between 2% and 25% of NaOH; at a temperature of from 10° C. to 90° C., advantageously from 10° C. to 80° C., preferably from 10° C. to 70° C., in particular from 10° C. to 60° C. According to one particular embodiment, step b) is carried out with a solution A comprising between 1% and 50% by weight, more preferentially between 2% and 40% by weight, in particular between 2% and 30%, more particularly between 2% and 25% of a salt of formula $Na_2SO_3$; between 1% and 50% by weight, more preferentially between 2% and 40% by weight, in particular between 2% and 30%, more particularly between 2% and 25% of KOH and between 1% and 50% by weight, more preferentially between 2% and 40% by weight, in particular between 2% and 30%, more particularly between 2% and 25% of NaOH; at a temperature of from 10° C. to 90° C., advantageously from 10° C. to 80° C., preferably from 10° C. to 70° C., in particular from 10° C. to 60° C.

Preferably, according to one preferred embodiment, step b) is carried out with an aqueous solution A comprising between 1% and 50% by weight, more preferably between 2% and 40% by weight, in particular between 2% and 30%, more particularly between 2% and 25% of a salt of formula $Y^{n+}_m SO_3$ and between 1% and 50% by weight, more preferentially between 2% and 40% by weight, in particular between 2% and 30%, more particularly between 2% and 25% of NaOH; at a temperature of from 10° C. to 90° C., advantageously from 10° C. to 80° C., preferably from 10° C. to 70° C., in particular from 10° C. to 60° C. According to one particular embodiment, step b) is carried out with an aqueous solution A comprising between 1% and 50% by weight, more preferentially between 2% and 40% by weight, in particular between 2% and 30%, more particularly between 2% and 25% of a salt of formula $Na_2SO_3$ and between 1% and 50% by weight, more preferentially between 2% and 40% by weight, in particular between 2% and 30%, more particularly between 2% and 25% of NaOH; at a temperature of from 10° C. to 90° C., advantageously from 10° C. to 80° C., preferably from 10° C. to 70° C., in particular from 10° C. to 60° C.

According to one preferred embodiment, step b) is carried out with an aqueous solution A comprising between 1% and 50% by weight, more preferably between 2% and 40% by weight, in particular between 2% and 30%, more particularly between 2% and 25% of a salt of formula $Y^{n+}_m SO_3$ and between 1% and 50% by weight, more preferentially between 2% and 40% by weight, in particular between 2% and 30%, more particularly between 2% and 25% of KOH; at a temperature of from 10° C. to 90° C., advantageously from 10° C. to 80° C., preferably from 10° C. to 70° C., in particular from 10° C. to 60° C. According to one particular embodiment, step b) is carried out with an aqueous solution A comprising between 1% and 50% by weight, more preferentially between 2% and 40% by weight, in particular between 2% and 30%, more particularly between 2% and 25% of a salt of formula $Na_2SO_3$ and between 1% and 50% by weight, more preferentially between 2% and 40% by weight, in particular between 2% and 30%, more particularly between 2% and 25% of KOH; at a temperature of from 10° C. to 90° C., advantageously from 10° C. to 80° C., preferably from 10° C. to 70° C., in particular from 10° C. to 60° C.

According to one preferred embodiment, step b) is carried out with an aqueous solution A comprising between 1% and 50% by weight, more preferably between 2% and 40% by weight, in particular between 2% and 30%, more particularly between 2% and 25% of a salt of formula $Y^{n+}_m SO_3$; between 1% and 50% by weight, more preferentially between 2% and 40% by weight, in particular between 2% and 30%, more particularly between 2% and 25% of KOH and between 1% and 50% by weight, more preferentially between 2% and 40% by weight, in particular between 2% and 30%, more particularly between 2% and 25% of NaOH; at a temperature of from 10° C. to 90° C., advantageously from 10° C. to 80° C., preferably from 10° C. to 70° C., in particular from 10° C. to 60° C. According to one particular embodiment, step b) is carried out with an aqueous solution A comprising between 1% and 50% by weight, more preferentially between 2% and 40% by weight, in particular between 2% and 30%, more particularly between 2% and 25% of a salt of formula $Na_2SO_3$; between 1% and 50% by weight, more preferentially between 2% and 40% by weight, in particular between 2% and 30%, more particularly between 2% and 25% of KOH and between 1% and 50% by weight, more preferentially between 2% and 40% by weight, in particular between 2% and 30%, more particularly between 2% and 25% of NaOH; at a temperature of from 10° C. to 90° C., advantageously from 10° C. to 80° C., preferably from 10° C. to 70° C., in particular from 10° C. to 60° C.

Alternatively, said solution A can be an organic solution containing a solvent. The solvent is defined as an inert organic compound wherein 1-chloro-3,3,3-trifluoropropene is at least partially soluble. The solvent is preferably selected from the group consisting of hydrocarbons, ethers, alcohols, alkyl halides, substituted or unsubstituted benzenes, alkyl nitrile, amides, sulfoxides, sulfones, phosphate esters and mixtures thereof. Preferably, the solvent is selected from ethers, alcohols, alkyl halides, substituted or unsubstituted benzenes, alkyl nitrile, amides, sulfoxides, sulfones, and mixtures thereof. The ethers include acyclic alkyl ethers, cyclic ethers, perfluorinated ethers, glyme, diglyme, triglyme, tetraglyme, and mixtures thereof. Acyclic alkyl ethers include dimethyl ether, ethyl ether, methyl ethyl ether, and mixtures thereof. The cyclic ethers include 2-methyltetrahydrofuran, tetrahydrofuran, tetrahydropyran, 1,4-dioxane, and mixtures thereof. The perfluorinated ethers include perfluoro-N-methyl morpholine, perfluorotetrahydrofuran, and mixtures thereof. The alcohols include alkyl alcohols, glycols, glycerol, and mixtures thereof. The alcohol alkyls include methanol, ethanol, propanol, isopropanol, 2-methyl-2-propanol, cyclohexanol, and mixtures thereof. Examples of glycol include ethylene glycol, propylene glycol, diethylene glycol, and mixtures thereof. The substituted or unsubstituted benzenes include alkylbenzenes, halobenzenes, benzonitrile phenol, anisole, biphenyl, nitrobenzene and mixtures thereof. The alkylbenzenes include toluene, ethylbenzene, o-xylene, m-xylene, p-xylene, mesitylene, durene, 2-phenylhexane, and mixtures thereof. The halobenzenes include fluorobenzene, chlorobenzene, 1,2-dichlorobenzene, 1,4-dichlorobenzene, and mixtures thereof. The alkyl halides include dichloromethane, chloroform, carbon tetrachloride, chloroethane, 1,2-dichloroethane, and mixtures thereof. The alkyl nitriles include acetonitrile, butyronitrile, methylglutaronitrile, adiponitrile, and mixtures thereof. The amides include N,N-dimethyl formamide, N,N-dimethylacetamide, N-methyl-2-pyrrolidone and mixtures thereof. The sulfoxides include dimethyl sulfoxide. The sulfones include sulfolane.

According to a second aspect of the present invention, a process for producing 1-chloro-3,3,3-trifluoropropene is provided; preferably, a process for producing trans-1-chloro-3,3,3-trifluoropropene.

Said process for producing 1-chloro-3,3,3-trifluoropropene comprises the steps of:

i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream B comprising 1-chloro-3,3,3-trifluoropropene, HF and HCl;

ii) carrying out the process for purifying 1-chloro-3,3,3-trifluoropropene according to the present invention using a stream comprising 1-chloro-3,3,3-trifluoropropene, HF and/or HCl.

Preferably, said process for producing trans-1-chloro-3,3,3-trifluoropropene comprises the steps of:

i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream B comprising trans-1-chloro-3,3,3-trifluoropropene, HF and HCl;

ii) carrying out the process for purifying trans-1-chloro-3,3,3-trifluoropropene according to the present invention using a stream comprising trans-1-chloro-3,3,3-trifluoropropene, HF and/or HCl.

In particular, said process for producing trans-1-chloro-3,3,3-trifluoropropene comprises the steps of:

i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream B comprising trans-1-chloro-3,3,3-trifluoropropene, cis-1-chloro-3,3,3-trifluoropropene, HF and HCl;

ii) carrying out the process for purifying trans-1-chloro-3,3,3-trifluoropropene according to the present invention using a stream comprising trans-1-chloro-3,3,3-trifluoropropene, cis-1-chloro-3,3,3-trifluoropropene, HF and/or HCl.

More particularly, in the stream B and in the stream used for carrying out step ii), the molar ratio between the trans and cis isomer of 1-chloro-3,3,3-trifluoropropene is from 2:1 to 50:1, preferably 5:1 to 50:1, in particular 9:1 to 50:1.

Preferably, said step i) is carried out in a liquid phase, preferably low in HF.

According to one preferred embodiment, said starting composition comprises at least 10% by weight of said at least one chlorinated compound, based on the total weight of said starting composition. Advantageously, said starting composition advantageously comprises at least 15% by weight of said at least one chlorinated compound, preferably at least 20% by weight of said at least one chlorinated compound, more preferably at least 25% by weight of said at least one chlorinated compounds, in particular at least 30% by weight of said at least one chlorinated compound, more particularly at least 35% by weight of said at least one chlorinated compound, preferentially at least 40% by weight of said at least one chlorinated compound, advantageously preferably at least 45% by weight of said at least one chlorinated compound, preferably preferentially at least 50% by weight of said at least one chlorinated compound, particularly preferably at least 55% by weight of said at least one chlorinated compound, based on the total weight of said starting composition.

Preferably, said starting composition comprises at least 60% by weight or at least 65% by weight or at least 70% by weight or at least 75% by weight or at least 80% by weight or at least 85% by weight or at least 90% by weight or at least 95% by weight or at least 99% by weight of said at least one chlorinated compound, based on the total weight of said starting composition.

According to one preferred embodiment, said at least one chlorinated compound is 1,1,3,3-tetrachloropropene (1230za). Said process therefore comprises a step i) of contacting hydrofluoric acid (HF) in a reactor with a starting composition comprising 1,1,3,3-tetrachloropropene (1230za) to produce a stream B comprising 1-chloro-3,3,3-trifluoropropene (1233zd), HF and HCl; said step i) is carried out in a low-HF liquid phase as defined below.

Preferably, the present process allows the production of 1-chloro-3,3,3-trifluoropropene in the form of a mixture of the two cis and trans isomers. The present process makes it possible to obtain mainly the trans isomer of 1-chloro-3,3,3-trifluoropropene; preferably, the stream B comprises at least 90 mol % of trans-1-chloro-3,3,3-trifluoropropene. In particular, the stream B comprises at least 95 mol % of trans-1-chloro-3,3,3-trifluoropropene.

Said starting composition therefore comprises at least 10% by weight of 1,1,3,3-tetrachloropropene, based on the total weight of said starting composition. Said starting composition advantageously comprises at least 15% by weight of 1,1,3,3-tetrachloropropene, preferably at least 20% by weight of 1,1,3,3-tetrachloropropene, more preferably at least 25% by weight of 1,1,3,3-tetrachloropropene, in particular at least 30% by weight of 1,1,3,3-tetrachloropropene, more particularly at least 35% by weight of 1,1,3,3-tetrachloropropene, preferentially at least 40% by weight of 1,1,3,3-tetrachloropropene, advantageously preferentially at least 45% by weight of 1,1,3,3-tetrachloropropene, preferably preferentially at least 50% by weight of 1,1,3,3-tetrachloropropene, particularly preferentially at least 55% by weight of 1,1,3,3-tetrachloropropene, based on the total weight of said starting composition. Said starting composition preferably comprises at least 60% by weight or at least 65% by weight or at least 70% by weight or at least 75% by weight or at least 80% by weight or at least 85% by weight or at least 90% by weight or at least 95% by weight or at least 99% by weight of 1,1,3,3-tetrachloropropene, based on the total weight of said starting composition.

According to one preferred embodiment, said starting composition comprises less than 15% by weight of HF, based on the total weight of said starting composition, advantageously less than 10% by weight of HF, preferably less than 8% by weight of HF, more preferably less than 6% by weight of HF, in particular less than 5% by weight of HF, more particularly less than 4% by weight of HF, preferentially less than 2% by weight of HF, based on the total weight of said starting composition. In the present process, preferably, the starting composition is devoid of HF. The term "devoid" signifies an amount by weight of less than 500 ppm, preferably less than 100 ppm, more particularly less than 10 ppm.

Said low-HF liquid phase is preferably a liquid phase comprising less than 15% by weight of HF, advantageously less than 10% by weight of HF, preferably less than 8% by weight of HF, more preferably less than 6% by weight of HF, in particular less than 5% by weight of HF, more particularly less than 4% by weight of HF, preferentially less than 2% by weight of HF, based on the total weight of said liquid phase.

While step i) is being carried out, said liquid phase may comprise at least 10% by weight of compounds of formula (I) $C_3H_nF_mCl_p$ (I) wherein n is an integer from 0 to 8, m is an integer from 0 to 8, and p is an integer from 0 to 8; preferably, n is an integer from 0 to 8, m is an integer from 0 to 6, and p is an integer from 0 to 6. Compounds of formula (I) may, for example, be $C_3Cl_6$, $C_3H_4Cl_4$ or $C_3H_3Cl_5$. Preferably, while step i) is being carried out, said liquid phase may comprise at least 10% by weight of compounds of formula (I) $C_3H_nF_mCl_p$ (I) wherein n is an integer from 1 to 8, m is an integer from 0 to 4, and p is an integer from 0 to 4; preferably, n is an integer from 1 to 4, m is an integer from 0 to 3, and p is an integer from 2 to 4. The compounds of formula (I) may be propane- or propene-type compounds comprising one or more chlorine atoms and/or one or more fluorine atoms. Said liquid phase may preferably comprise at least 10% by weight of compounds of formula (I) selected from the group consisting of $C_3H_2Cl_4$, $C_3H_2Cl_3F$, $C_3H_2Cl_2F_2$, $C_3H_3Cl_5$, $C_3H_3Cl_4F$, $C_3H_3Cl_3F_2$, and $C_3H_3Cl_2F_3$. In particular, said liquid phase may comprise at least 10% by weight of compounds of formula (I) selected from the group consisting of $C_3H_2Cl_4$, $C_3H_2Cl_3F$, and $C_3H_2Cl_2F_2$. Said liquid phase may comprise at least 15% by weight of compounds of formula (I) $C_3H_nF_mCl_p$ (I) wherein n is an integer from 0 to 8, m is an integer from 0 to 8, and p is an integer from 0 to 8; preferably, n is an integer from 0 to 8, m is an integer from 0 to 6, and p is an integer from 0 to 6. More particularly, while step i) is being carried out, said liquid phase may comprise at least 15% by weight of compounds of formula (I) $C_3H_nF_mCl_p$ (I) wherein n is an integer from 1 to 8, m is an integer from 0 to 4, and p is an integer from 0 to 4; preferably, n is an integer from 1 to 4, m is an integer from 0 to 3, and p is an integer from 2 to 4. Said liquid phase may preferably comprise at least 15% by weight of compounds of formula (I) selected from the group consisting of $C_3H_2Cl_4$, $C_3H_2Cl_3F$, $C_3H_2Cl_2F_2$, $C_3H_3Cl_3$, $C_3H_3Cl_4F$, $C_3H_3Cl_3F_2$, and $C_3H_3Cl_2F_3$. In particular, said liquid phase may comprise at least 15% by weight of compounds of formula (I) selected from the group consisting of $C_3H_2Cl_4$, $C_3H_2Cl_3F$, and $C_3H_2Cl_2F_2$. Said liquid phase may comprise at least 20%, at least 30%, at least 40%, at least 50%, at least 60%, at least 70%, at least 80% or at least 90% by weight of compounds of formula (I) $C_3H_nF_mCl_p$ (I) wherein n is an integer from 0 to 8, m is an integer from 0 to 8, and p is an integer from 0 to 8; preferably, n is an integer from 0 to 8, m is an integer from 0 to 6, and p is an integer from 0 to 6. Said liquid phase may comprise at least 20%, at least 30%, at least 40%, at least 50%, at least 60%, at least 70%, at least 80% or at least 90% by weight of compounds of formula (I) $C_3H_nF_mCl_p$ (I) wherein n is an integer from 1 to 8, m is an integer from 0 to 4, and p is an integer from 0 to 4; preferably, n is an integer from 1 to 4, m is an integer from 0 to 3, and p is an integer from 2 to 4. Said liquid phase may preferably comprise at least 20%, at least 30%, at least 40%, at least 50%, at least 60%, at least 70%, at least 80% or at least 90% by weight of compounds of formula (I) selected from the group consisting of $C_3H_2Cl_4$, $C_3H_2Cl_3F$, $C_3H_2Cl_2F_2$, $C_3H_3Cl_5$, $C_3H_3Cl_4F$, $C_3H_3Cl_3F_2$, and $C_3H_3Cl_2F_3$. In particular, said liquid phase may comprise at least 20%, at least 30%, at least 40%, at least 50%, at least 60%, at least 70%, at least 80% or at least 90% by weight of compounds of formula (I) selected from the group consisting of $C_3H_2Cl_4$, $C_3H_2Cl_3F$, and $C_3H_2Cl_2F_2$.

Step i) is preferably carried out in the absence of catalyst.

Step i) may alternatively be carried out in the presence of a catalyst. The catalyst may be a $TiCl_4$ or $SbCl_5$ catalyst. The catalyst may also be an ionic liquid. The ionic liquids which may be suitable are Lewis acid derivatives based on aluminum, titanium, niobium, tantalum, tin, antimony, nickel, zinc or iron. The term "ionic liquids" refers to nonaqueous salts of ionic nature which are liquid at moderate temperatures (preferably below 120° C.). Ionic liquids preferably result from the reaction between an organic salt and an inorganic compound. Ionic liquids are preferably obtained by reaction of at least one halogen or oxyhalogen Lewis acid based on aluminum, titanium, niobium, tantalum, tin, antimony, nickel, zinc or iron with a salt of general formula $Y^+A^-$ wherein $A^-$ denotes a halide anion (bromide, iodide and, preferably, chloride or fluoride) or hexafluoroantimonate ($SbF_6^-$) and $Y^+$ a quaternary ammonium, quaternary phosphonium or ternary sulfonium cation. The halogen Lewis acid based on aluminum, titanium, niobium, tantalum, antimony, nickel, zinc or iron may be a chloro, bromo, fluoro or mixed derivative, for example a chlorofluoro acid. Mention may be made more particularly of the chlorides, fluorides or chlorofluorides having the following formulae:

$TiCl_xF_y$ with $x+y=4$ and $0<=x<=4$ $TaCl_xF_y$ with $x+y=5$ and $0<=x<=5$ $NbCl_xF_y$ with $x+y=5$ and $0<=x<=5$ $SnCl_xF_y$ with $x+y=4$ and $1<=x<=4$ $SbCl_xF_y$ with $x+y=5$ and $0<=x<=5$ $AlCl_xF_y$ with $x+y=3$ and $0<=x<=3$ $NiCl_xF_y$ with $x+y=2$ and $0<=x<=2$ $FeCl_xF_y$ with $x+y=3$ and $0<=x<=3$ As examples of such compounds, mention may be made of the following compounds: $TiCl_4$, $TiF_4$, $TaCl_5$, $TaF_5$, $NbCl_5$, $NbF_5$, $SbCl_5$, $SbCl_4F$, $SbCl_3F_2$, $SbCl_2F_3$, $SbClF_4$, $SbF_5$, and mixtures thereof. The following compounds are preferentially used: $TiCl_4$, $TaCl_5+TaF_5$, $NbCl_5+NbF_5$, $SbCl_5$, $SbFCl_4$, $SbF_2Cl_3$, $SbF_3Cl_2$, $SbF_4Cl$, $SbF_5$, and $SbCl_5+SbF_5$. The antimony-based compounds are more particularly preferred. As examples of oxyhalogen Lewis acids that may be used according to the invention, mention may be made of $TiOCl_2$, $TiOF_2$ and $SbOCl_xF_y$ (x+y=3). In the salt $Y^{30}A^-$, the cation $Y^+$ may correspond to one of the following general formulae: $R^1R^2R^3R^4N^+$, $R^1R^2R^3R^4P^+$, $R^1R^2R^3S^+$ wherein the symbols $R^1$ to $R^4$, which may be identical or different, each denote a saturated or unsaturated, cyclic or noncyclic, or aromatic hydrocarbyl, chlorohydrocarbyl, fluorohydrocarbyl, chlorofluorohydrocarbyl or fluorocarbyl group having from 1 to 10 carbon atoms, with one or more of these groups possibly also containing one or more heteroatoms such as N, P, S or O. The ammonium, phosphonium or sulfonium cation $Y^+$ may also form part of a saturated or unsaturated, or aromatic, heterocycle having from 1 to 3 nitrogen, phosphorus or sulfur atoms, and may correspond to one or other of the following general formulae:

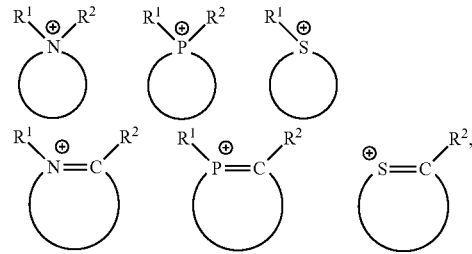

[Chem 1]

wherein $R^1$ and $R^2$ are as defined previously. A salt containing two or three ammonium, phosphonium or sulfonium sites in its formula may also be suitable for use. As examples of salts $Y^+A^-$, mention may be made of tetraalkylammonium chlorides and fluorides, tetraalkylphosphonium chlorides and fluorides, and trialkylsulfonium chlorides and fluorides, alkylpyridinium chlorides and fluorides, dialkylimidazolium chlorides, fluorides and bromides, and trialkylimidazolium chlorides and fluorides. Trimethylsulfonium fluoride or chloride, N-ethylpyridinium chloride or fluoride, N-butylpyridinium chloride or fluoride, 1-ethyl-3-methylimidazolium chloride or fluoride, and 1-butyl-3-methylimidazolium chloride or fluoride are more particularly valued. The ionic liquids may be prepared in a manner known per se by appropriate mixing of the halogen or oxyhalogen Lewis acid and the organic salt $Y^+A^-$. Reference may be made notably to the method described in document WO 01/81353. The catalyst may alternatively be triflic or trifluoroacetic acid as stated in U.S. Pat. No. 6,166,274.

According to one preferred embodiment, in addition to the trans/cis-1-chloro-3,3,3-trifluoropropene, the stream B comprises coproducts selected from the group consisting of 1,3,3,3-tetrafluoropropene and 1,1,1,3,3-pentafluoropropane. According to one preferred embodiment, the amount, in the stream B, of coproducts selected from the group consisting of 1,3,3,3-tetrafluoropropene and 1,1,1,3,3-pentafluoropropane is less than 0.5 mol %. The 1,3,3,3-tetrafluoropropene content in said stream B is preferably less than 0.5 mol %, more preferentially less than 0.4 mol %, more particularly less than 0.3 mol %. The 1,1,1,3,3-pentafluoropropane content in said stream B is preferably less than 0.1 mol %, more preferentially less than 0.075 mol %, more particularly less than 0.05 mol %.

Step i) is preferably carried out at a temperature of 50° C. to 150° C., preferably at a temperature of 75° C. to 100° C.

Step i) is preferably carried out at a pressure of 5 to 20 bara, preferably at a pressure of 10 to 18 bara, more particularly of 12 to 18 bara.

The molar HF/[chlorinated compounds] ratio at the entry of the reactor is preferably between 5 and 10, more preferably between 5 and 7, more particularly between 5 and 6. More particularly, when said chlorinated compound in the starting composition is 1,1,3,3-tetrachloropropene (1230za), the molar HF/1230za ratio is between 5 and 10, more preferably between 5 and 7, more particularly between 5 and 6.

The hydrofluoric acid and said starting composition can be introduced into the reactor via a static mixer. Preferably, the hydrofluoric acid is heated before it is introduced into the reactor and thus before the implementation of step i). Preferably, the hydrofluoric acid is heated to a temperature of from 100° C. to 170° C., preferably from 120° C. to 170° C., in particular from 125° C. to 165° C., more particularly from 125° C. to 155° C.

According to one particular embodiment, the stream B obtained in step i) can be subjected to purification steps prior to the implementation of step ii). Alternatively, the stream B obtained in step i) can be used directly in step ii).

Thus, said production process can comprise a step i'), subsequent to step i) and prior to step ii), comprising a step of treating the stream B to give a stream B1 comprising 1-chloro-3,3,3-trifluoropropene, HCl and HF and a stream B2 comprising at least 50% by weight of HF, for example preferably at least 70% by weight of HF. The treatment step (i') is preferably a reflux column, carried out advantageously at a temperature of between 30 and 120° C. to give the stream B2, which is recycled to the reactor. Preferably, in the stream B1, the molar ratio between the trans and cis isomer of 1-chloro-3,3,3-trifluoropropene is from 2:1 to 50:1, preferably 5:1 to 50:1, in particular 9:1 to 50:1.

According to one particular embodiment, said process for producing 1-chloro-3,3,3-trifluoropropene according to the present invention comprises the steps of:

i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream B comprising 1-chloro-3,3,3-trifluoropropene, HF and HCl;

i') a step of treating the stream B to give a stream B1 comprising 1-chloro-3,3,3-trifluoropropene, HCl and HF and a stream B2 comprising at least 50% by weight of HF;

ii) carrying out the process for purifying 1-chloro-3,3,3-trifluoropropene according to the present invention starting from the stream B1 obtained in step i').

The present production process can also comprise a step ii') subsequent to step i') and prior to step ii). Preferably, said step ii') is a step of recovering hydrochloric acid from the stream B1 to form a stream B3 of HCl and a stream B4 comprising 1-chloro-3,3,3-trifluoropropene, HCl and HF. The recovery of HCl in step (ii') is preferably obtained by means of a distillation column equipped with a bottom reboiler and a top reflux system. The temperature at the bottom is advantageously between 20 and 110° C. The temperature at the top is advantageously between −50 and 0° C. The distillation of HCl is typically performed at a pressure of between 7 and 25 bar. This recovery step makes it possible to obtain a stream B4 wherein the amount of HCl is greatly reduced compared to the amount of HCl in the stream B1.

Thus, according to one particular embodiment, said process for producing 1-chloro-3,3,3-trifluoropropene according to the present invention comprises the steps of:

i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream B comprising 1-chloro-3,3,3-trifluoropropene, HF and HCl;

i') treating the stream B to give a stream B1 comprising 1-chloro-3,3,3-trifluoropropene, HCl and HF and a stream B2 comprising at least 50% by weight of HF;

ii') recovering hydrochloric acid from the stream B1 to form a stream B3 of HCl and a stream B4 comprising 1-chloro-3,3,3-trifluoropropene, HCl and HF;

ii) carrying out the process for purifying 1-chloro-3,3,3-trifluoropropene according to the present invention from the stream B4 obtained in step ii') to form the neutralized stream A1.

Preferably, in the stream B4, the molar ratio between the trans and cis isomer of 1-chloro-3,3,3-trifluoropropene is from 2:1 to 50:1, preferably 5:1 to 50:1, in particular 9:1 to 50:1.

The present production process can also comprise a step iii') subsequent to step ii') and prior to step ii). Preferably, step iii') is a step of separating to form a stream B5 comprising at least 90% by weight, preferably at least 98% by weight and in particular at least 99% by weight of HF, and a stream B6 comprising 1-chloro-3,3,3-trifluoropropene, HCl and HF. The separation step is preferably a decantation, carried out at a temperature advantageously of between −50 and 50° C., preferably between −20° C. and 10° C.

Thus, according to one particular embodiment, said process for producing 1-chloro-3,3,3-trifluoropropene according to the present invention comprises the steps of:

i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream B comprising 1-chloro-3,3,3-trifluoropropene, HF and HCl;

i') treating the stream B to give a stream B1 comprising 1-chloro-3,3,3-trifluoropropene, HCl and HF and a stream B2 comprising at least 50% by weight of HF;

ii') recovering hydrochloric acid from the stream B1 to form a stream B3 of HCl and a stream B4 comprising 1-chloro-3,3,3-trifluoropropene, HCl and HF;

iii') separating the stream B4 obtained in step ii') to form a stream B5 comprising at least 90% by weight and a stream B6 comprising 1-chloro-3,3,3-trifluoropropene, HCl and HF;

ii) carrying out the process for purifying 1-chloro-3,3,3-trifluoropropene according to the present invention from the stream B6 obtained in step iii') to form the neutralized stream A1.

Preferably, in the stream B6, the molar ratio between the trans and cis isomer of 1-chloro-3,3,3-trifluoropropene is from 2:1 to 50:1, preferably 5:1 to 50:1, in particular 9:1 to 50:1.

The present production process can also comprise a step iv') subsequent to step iii') and prior to step ii). Preferably, step iv') is a step of washing with water. This step eliminates part of the HCl and of the HF contained in the stream B6.

Thus, according to one particular embodiment, said process for producing 1-chloro-3,3,3-trifluoropropene according to the present invention comprises the steps of:

i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream B comprising 1-chloro-3,3,3-trifluoropropene, HF and HCl;

i') treating the stream B to give a stream B1 comprising 1-chloro-3,3,3-trifluoropropene, HCl and HF and a stream B2 comprising at least 50% by weight of HF;

ii') recovering hydrochloric acid from the stream B1 to form a stream B3 of HCl and a stream B4 comprising 1-chloro-3,3,3-trifluoropropene, HCl and HF;

iii') separating the stream B4 obtained in step ii') to form a stream B5 comprising at least 90% by weight and a stream B6 comprising 1-chloro-3,3,3-trifluoropropene, HCl and HF;

iv') washing of said stream B6 obtained in step iii') with water to form a stream B7 comprising 1-chloro-3,3,3-trifluoropropene and an acidic aqueous solution B8;

ii) carrying out the process for purifying 1-chloro-3,3,3-trifluoropropene according to the present invention from the stream B7 obtained in step iv') to form the neutralized stream A1.

Preferably, in the stream B7, the molar ratio between the trans and cis isomer of 1-chloro-3,3,3-trifluoropropene is from 2:1 to 50:1, preferably 5:1 to 50:1, in particular 9:1 to 50:1.

The present production process can also comprise a step iii) subsequent to step ii). Preferably, step iii) consists in drying said neutralized stream A1 comprising 1-chloro-3,3,3-trifluoropropene to form a dried stream A2 comprising 1-chloro-3,3,3-trifluoropropene. The drying step can be carried out using a molecular sieve, zeolite, inorganic salts such as calcium sulfate or calcium chloride, silica gel, activated carbon. Examples of molecular sieves and of zeolites are described in document WO 2017/050686. Examples of inorganic salts, of molecular sieves, of silica gel and of activated carbon are also described in WO 2017/031406. Examples of molecular sieves, of activated carbon and of silica gel are also described in WO 2016/148957. Preferably, the drying step will be carried out using a molecular sieve, in particular using a 3A molecular sieve.

The present production process can also comprise a step iv) subsequent to step iii). Preferably, step iv) comprises one or more steps of distilling said stream A2 obtained in step iii).

Thus, according to one particular embodiment, said process for producing 1-chloro-3,3,3-trifluoropropene according to the present invention comprises the steps of:

i) bringing the hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream B comprising 1-chloro-3,3,3-trifluoropropene, HF and HCl;

i') treating the stream B to give a stream B1 comprising 1-chloro-3,3,3-trifluoropropene, HCl and HF and a stream B2 comprising at least 50% by weight of HF;

ii') recovering hydrochloric acid from the stream B1 to form a stream B3 of HCl and a stream B4 comprising 1-chloro-3,3,3-trifluoropropene, HCl and HF;

iii') separating the stream B4 obtained in step ii') to form a stream B5 comprising at least 90% by weight and a stream B6 comprising 1-chloro-3,3,3-trifluoropropene, HCl and HF;

iv') washing of said stream B6 obtained in step iii') with water to form a stream B7 comprising 1-chloro-3,3,3-trifluoropropene and an acidic aqueous solution B8;

ii) carrying out the process for purifying 1-chloro-3,3,3-trifluoropropene according to the present invention from the stream B7 obtained in step iv') to form the neutralized stream A1;

iii) drying of said neutralized stream A1 comprising 1-chloro-3,3,3-trifluoropropene to form a dried stream A2 comprising 1-chloro-3,3,3-trifluoropropene; and iv) distilling said stream A2 using one or more distillation columns to form a stream A3 comprising 1-chloro-3,3,3-trifluoropropene.

Preferably, in the stream B1, B4, B6 and B7, the molar ratio between the trans and cis isomer of 1-chloro-3,3,3-trifluoropropene is from 2:1 to 50:1, preferably 5:1 to 50:1, in particular 9:1 to 50:1.

Preferably, said production process according to the present invention is carried out continuously.

EXAMPLES

The examples below aim to study the behavior of a stream comprising in particular trans-1-chloro-3,3,3-trifluoropropene in the presence of different basic solutions. The examples are carried out in a reactor surmounted by a scrubbing column (both being heat insulated). The scrubbing column (internal diameter=24 mm, height=300 mm) is packed with Raschig rings (internal diameter 3 mm, external diameter=5 mm, length=5 mm, fraction of life in the packed column=63%). A basic solution was introduced and was turned in circles through a scrubbing column packed with Raschig rings (about 185 ml/min). The basic solution is brought to a temperature of 30° C. A stream comprising 1-chloro-3,3,3-trifluoropropene (95.5 mol % of the trans isomer and 2.5 mol % of the cis isomer) was then introduced into the reactor at a flow rate of 5 g/h. The gas stream was recovered after neutralization in order to be be dried over anhydrous $CaCl_2$ and trapped using a liquid nitrogen trap. The gas stream was analyzed by gas chromatography. The amount of trifluoropropyne formed after neutralization is determined in order to evaluate the impact of the basic solutions tested on 1-chloro-3,3,3-trifluoropropene. Three basic solutions were tested and the results are shown below in table 1.

TABLE 1

| Example | Basic solution | Trifluoropropyne content |
|---|---|---|
| Example 1 (Comp.) | 5% KOH | 3840 ppm |
| Example 2 (Comp.) | 5% NaOH | 2410 ppm |
| Example 3 (Inv.) | 5% NaOH + 5% $Na_2SO_3$ | 1830 ppm |

As demonstrated by the examples above, the use of a basic solution comprising a sulfite salt and an alkali metal hydroxide makes it possible to limit the formation of trifluoropropyne during the neutralization step. The process according to the present invention is consequently more efficient than a process implementing a neutralization step in the presence of KOH or NaOH alone.

The invention claimed is:

1. A process for purifying 1-chloro-3,3,3-trifluoropropene comprising the steps of:
    a) providing a stream comprising 1-chloro-3,3,3-trifluoropropene and at least one compound of formula HX wherein X is F or Cl;
    b) bringing the stream from step a) into contact with a solution A comprising at least one alkali metal hydroxide or one alkaline-earth metal hydroxide and at least one sulfite salt of formula $Y^{n+}{}_mSO_3$ wherein Y is an alkali or alkaline-earth metal, n=1 or 2, and m=2 when n=1 or m=1 when n=2; in order to form a neutralized stream A1 comprising 1-chloro-3,3,3-trifluoropropene.

2. The process as claimed in claim 1, wherein said at least one sulfite salt is selected from the group consisting of $Na_2SO_3$, $K_2SO_3$, $Li_2SO_3$, $CaSO_3$ and $MgSO_3$ or a mixture thereof.

3. The process as claimed in claim 1, wherein said at least one sulfite salt is $Na_2SO_3$ or $K_2SO_3$ or a mixture of both.

4. The process as claimed in claim 1, wherein said solution A comprises at least one alkali metal hydroxide.

5. The process as claimed in claim 1, wherein said solution A of step b) comprises NaOH and $Na_2SO_3$.

6. The process as claimed in claim 1, wherein said solution A of step b) is an aqueous solution.

7. The process as claimed in claim 1, wherein the content of said at least one sulfite salt is between 2 and 25% by weight based on the total weight of said solution A.

8. The process as claimed in claim 1, wherein step b) is carried out at a temperature of 10° C. to 70° C.

9. The process as claimed in claim 1, wherein the content of alkali metal hydroxide or alkaline-earth metal hydroxide is between 2 and 25% by weight based on the total weight of said solution A.

10. The process as claimed in claim 1, wherein step b) is carried out with an aqueous solution A comprising from 3 to 10% of $Na_2SO_3$ and from 3 to 10% NaOH; and at a temperature of from 20° C. to 60° C.

11. The process as claimed in claim 1, wherein, in the stream provided in step a), the molar ratio between the trans isomer and the cis isomer of 1-chloro-3,3,3-trifluoropropene is from 2:1 to 50:1.

12. A process for producing 1-chloro-3,3,3-trifluoropropene comprising the steps of:
    i. bringing hydrofluoric acid (HF) into contact, in a reactor, with a starting composition comprising at least one chlorinated compound selected from the group consisting of 1,1,3,3-tetrachloropropene, 1,3,3,3-tetrachloropropene and a mixture of the two, to obtain a stream B comprising 1-chloro-3,3,3-trifluoropropene, HF and/or HCl;
    ii. carrying out the process for purifying 1-chloro-3,3,3-trifluoropropene according to claim 1 using a stream comprising 1-chloro-3,3,3-trifluoropropene, HF and/or HCl.

* * * * *